Figure 1:
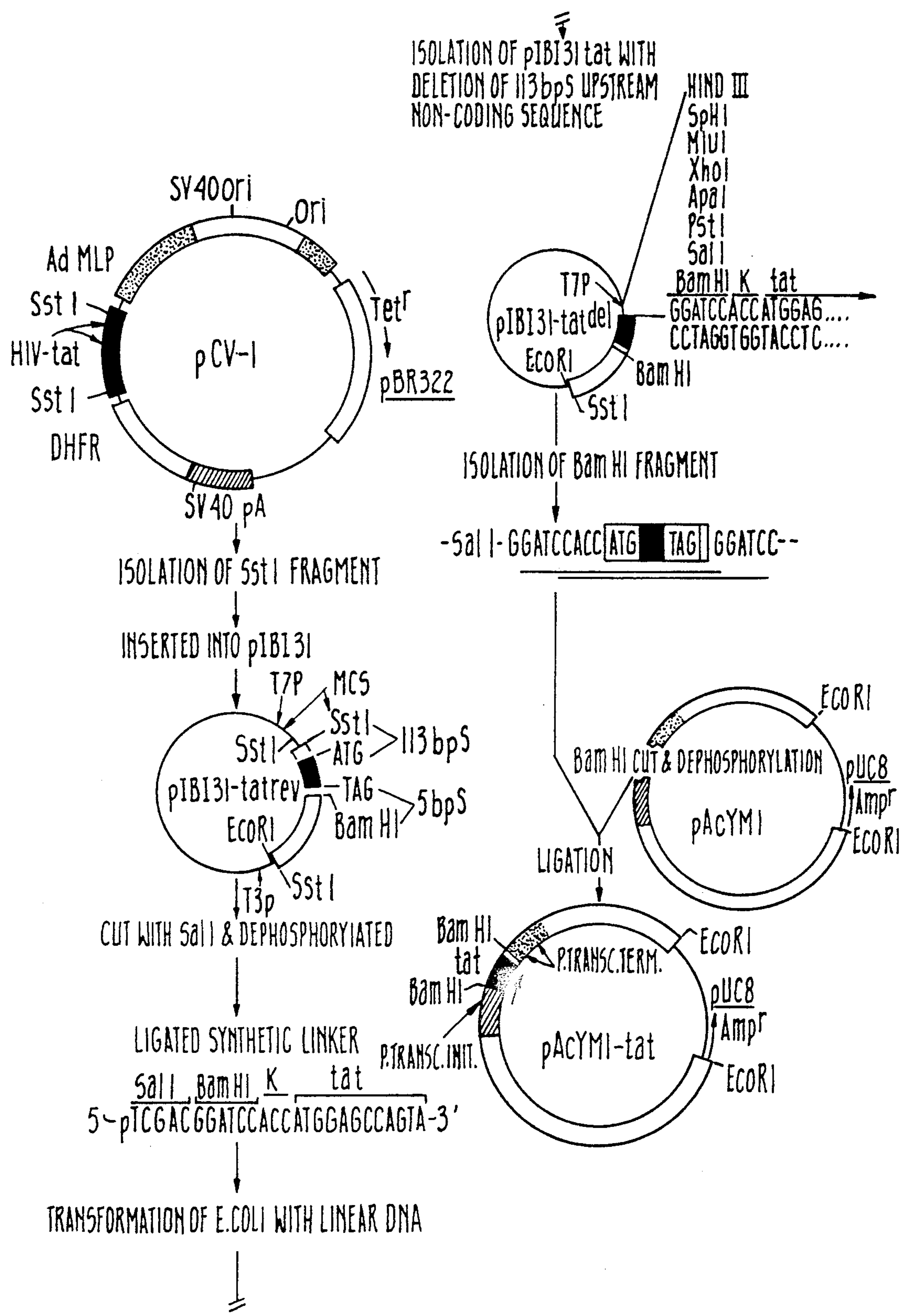

US005278042A

United States Patent [19]

Wong-Staal et al.

[11] Patent Number: 5,278,042

[45] Date of Patent: Jan. 11, 1994

[54] METHOD FOR DETECTING INHIBITORS OF TAT PROTEIN

[75] Inventors: Flossie Wong-Staal; Jay Rappaport, both of Rockville, Md.; James R. Rusche, Framingham, Mass.

[73] Assignee: The United States of America as represented by the Department of Health & Human Services, Bethesda, Md.

[21] Appl. No.: 306,612

[22] Filed: Feb. 6, 1989

[51] Int. Cl.[5] ........................................ G01N 33/569

[52] U.S. Cl. ........................................ 435/5; 435/7.1; 530/350

[58] Field of Search .................... 730/350; 435/5, 7.1, 435/974

[56] References Cited

PUBLICATIONS

Muesing et al: Regulation of mRNA Accumulation by HIV trans-Activator Protein, Cell v48, pp. 691-701, Feb. 27, 1987.

Wu, F. et al (I) Alterations in Binding Char . . . Enhancer Factor J. of Virology Jan. '88 pp. 218-225.

Wu, F. et al, (II) Purification of . . . EBP-1 and UBP-1 EMBO Journal vol. 7 #7 pp. 2117-2129 Jul. '88.

*Primary Examiner*—Christine M. Nucker
*Assistant Examiner*—Jeffrey Stucker
*Attorney, Agent, or Firm*—Knobbe, Martens, Olson & Bear

[57] ABSTRACT

A method for evaluating the inhibitory effect of a substance on tat-protein TAR RNA binding is described. A test system for determining the association of tat-protein with TAR RNA is also included within the scope of the invention.

3 Claims, 7 Drawing Sheets

1 2 3 4

Fig. 3

METHOD FOR DETECTING INHIBITORS OF TAT PROTEIN

INTRODUCTION

It has been shown that HIV gene expression is regulated by the viral transregulatory protein known as tat. As taught herein, tat protein may now be used in binding assays to screen substances for use as tat inactivators. Such inactivators would be useful in treatment of acquired immunodeficiency syndrome (AIDS).

BACKGROUND OF THE INVENTION

It has been known that HIV-1 gene expression is positively regulated by the viral transregulatory protein, tat (Arya, et al., 1985, Sodroski, et al., 1985). Tat protein is an 86 amino acid polypeptide that is translated from doubly spliced mRNA containing one 5' non-coding exon and two coding exons. Tat expression is believed to be essential for HIV replication, since mutants lacking tat fail to produce significant levels of viral protein and mRNA. A "tat activation response" element, termed TAR, has been localized within the long terminal repeat (LTR), by deletion analysis, to the region −17 to +80 nucleotides relative to the transcription initiation site (Rosen, et al., 1985). The function of this element is position and orientation dependent and can confer tat inducibility to heterologous promotors, albeit to a reduced level.

DESCRIPTION OF THE INVENTION

It is the purpose of this invention to provide an assay which will indicate inhabition of binding of tat protein to TAR.

It is a further purpose of this invention to provide a method for evaluating agents which bind tat as a means of identifying useful therapeutic agents.

It is a further purpose of this invention to provide reliable methods for producing large amounts of tat protein.

FIGURES

FIG. 1: Construction of the baculovirus transfer vector pAcYM1-tat is illustrated. The Bam H1 fragment derived from pIBI31-tat, used to construct pAcYM1-tat, was inserted in the *E. coli* expression vector pREV as in U.S. Pat. No. 4,721,671, which is incorporated herein by reference.

Figure 2:
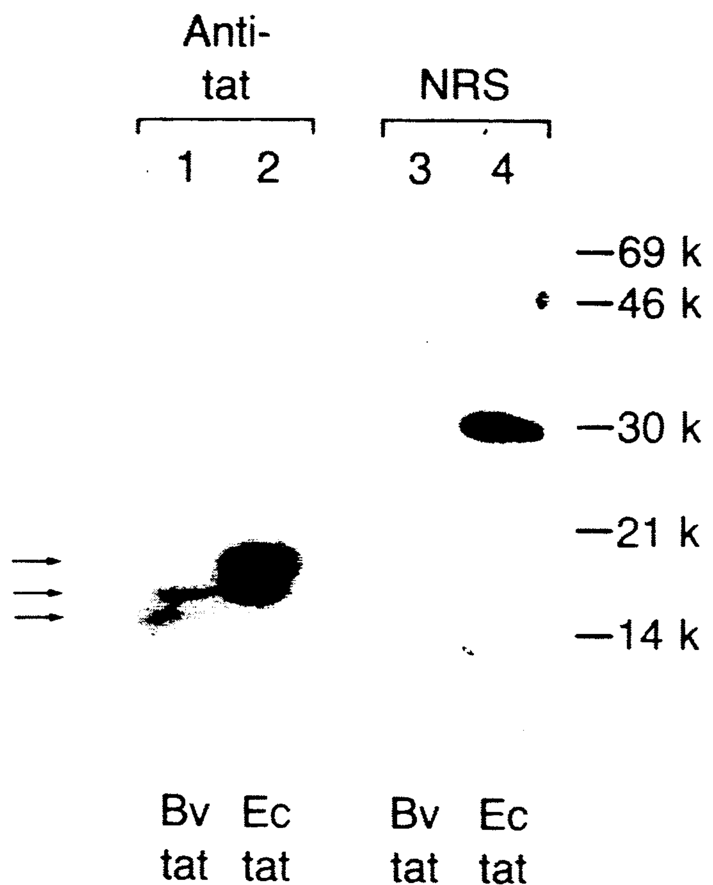

FIG. 2: Extract preparations of both *E. coli* and baculovirus systems containing tat protein was determined by Western Blot analysis.

Figure 3:
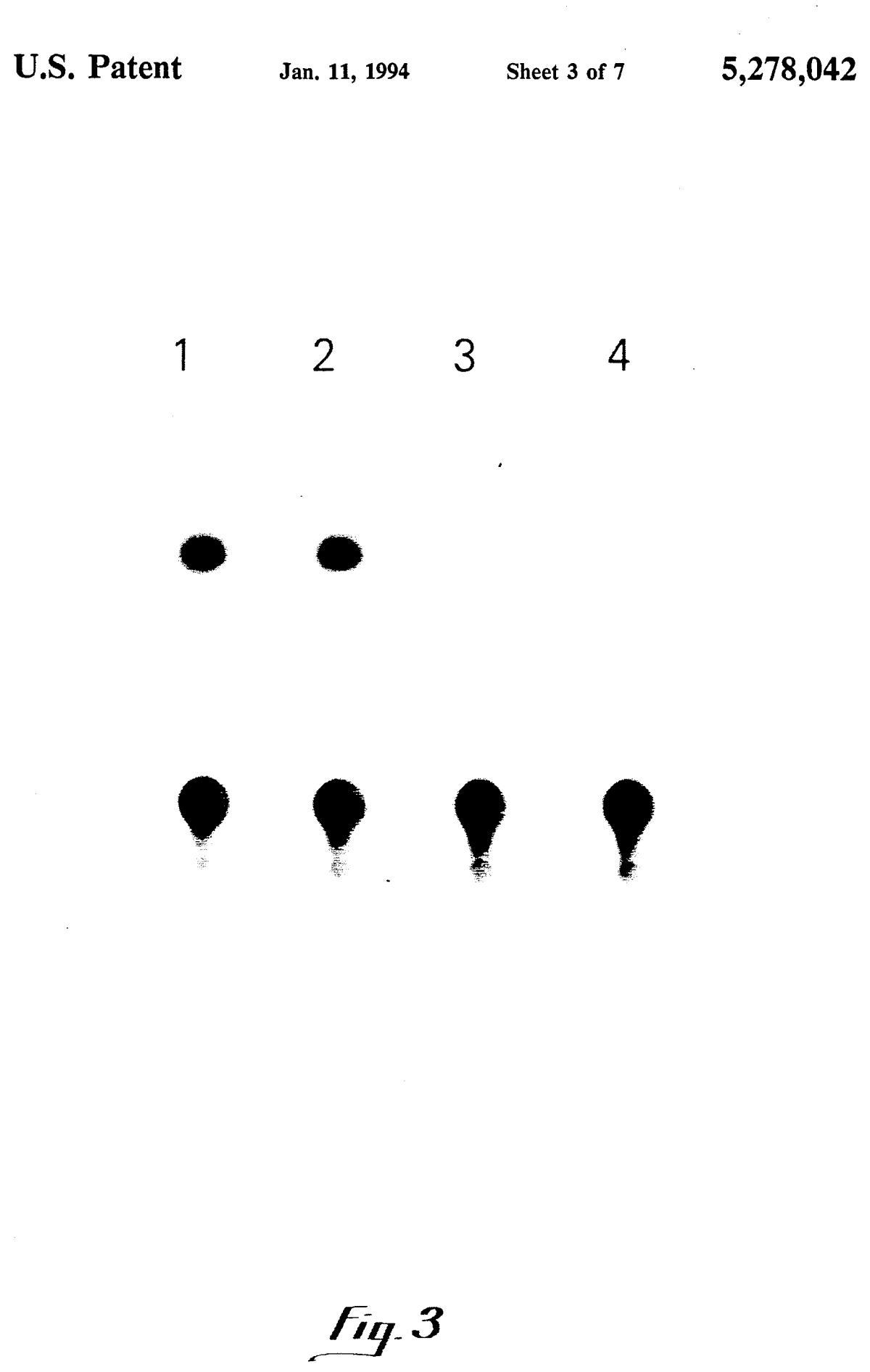

FIG. 3: Functional activity of both baculovirus and *E. coli* preparations were evaluated for functional activity as determined by induced level of CAT activity.

Figure 4:
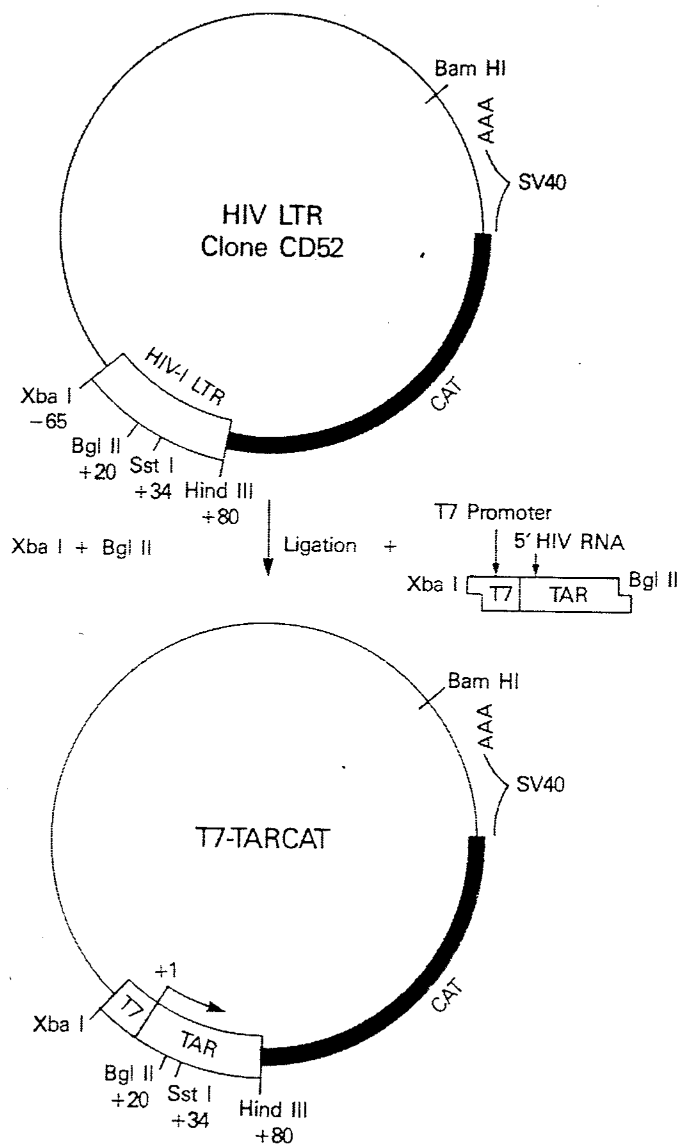

FIG. 4: A construct which substituted the upstream LTR sequences with the bacteriophage T7 polymerase promotor is illustrated.

Figure 5:
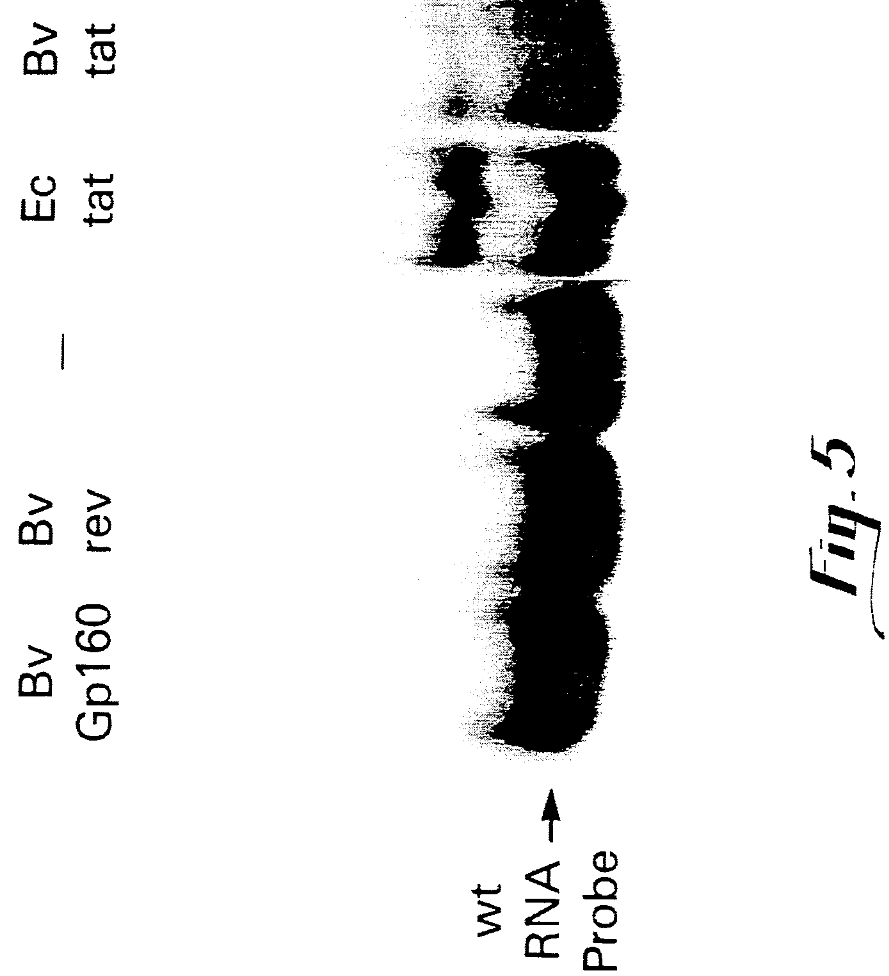

FIG. 5: Assay of direct binding ar shown using $^{32}P$ labeled 80 nt transcript in RNA gel mobility shift experiments of recombinant tat. Retarded bands represent protein-RNA complexes with *E.coli* tat and baculovirus tat extracts. Note comparison with activity with baculovirus preparations of pg160 and rev.

Figure 6:
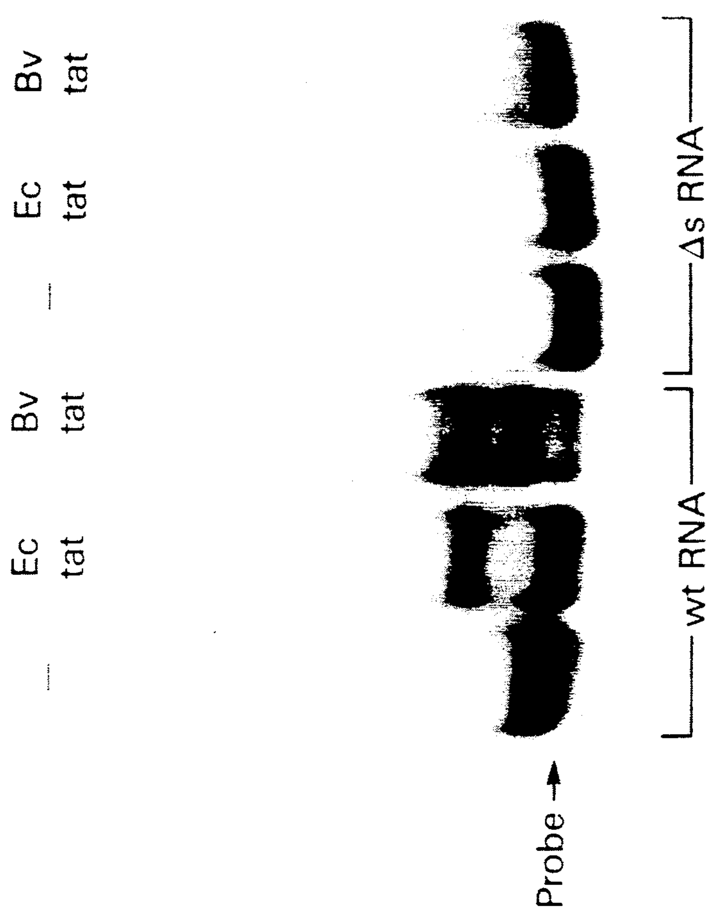

FIG. 6: Specificity of binding reaction is determined with RNA gel mobility shift assay using wild type and mutant transcripts.

Figure 7:
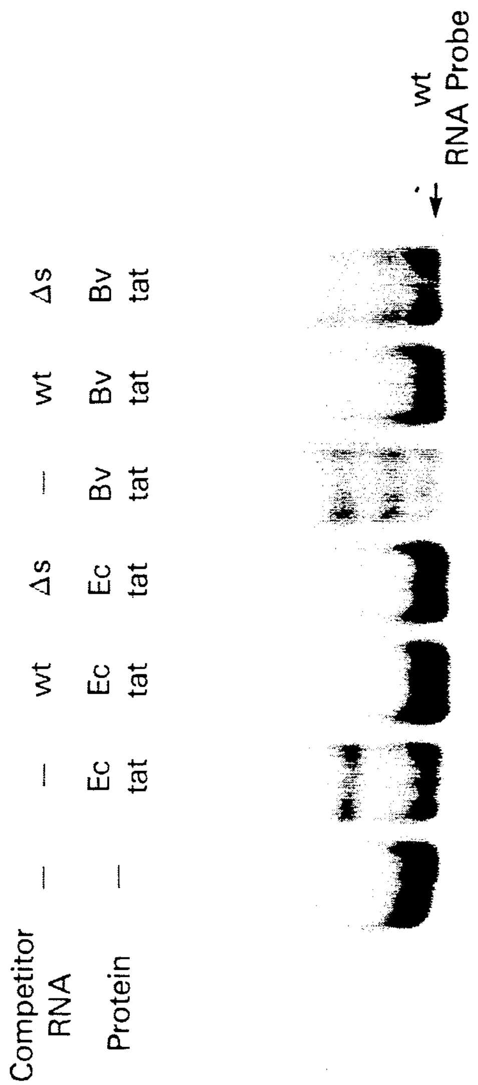

FIG. 7: Binding to RNA by excess unlabeled wt TAR RNA is completed as illustrated.

Since sequences which are responsive to tat are present immediately downstream of the transcription initiation site, tat was believed to interact directly or indirectly with these sequences at either the DNA or RNA level, or both. It had been predicted that the 5' untranslated region of HIV-1 mRNA formed a highly stable stem loop structure (Okomoto and Wong-Staal, 1986, Feng and Holland, 1988). The limits of TAR within HIV-1 and HIV-2 RNA include one and three stem loops, respectively. It had been known that while little overall sequence homology exists between HIV-1 and HIV-1 TAR, the stem-loop structure, as well as the pentanucleotide repeat sequence within the predicted loop, CTGGG, are maintained. Site directed mutagenesis of the pentamucleotide motif has demonstrated the requirement of the sequence (CTGGG) for tat transactivation. In addition to the requirement for recognition of sequences within the predicted TAR loop, complementarity of the bases forming the stem appeared to be essential. It is believed that this is the reason that the 3' border of the TAR region, as determined by progressive deletions, has been mapped to +44. Deletions extending further 5' could diminish base complementarity beyond a critical level needed for formation of RNA stem loop structure. (While these findings, taken together support the notion that RNA is a target in the tat transactivation, the possibility remains that sequences within TAR are required for interaction at the DNA level with transregulatory factors through the formation of cruciform structures.)

EXAMPLE 1

In order to investigate the mechanism of tat activation, recombinant tat was produced in both *E. coli* and baculovirus expression systems. The construction of the baculovirus transfer vector pAcYM1-tat is illustrated in FIG. 1. The same Bam HI fragment derived from pIBI31-tat, used to construct pAcYM1-tat was inserted into the *E. coli* expression vector pREV (U.S. Pat. No. 4,721,671). In this construction, tat was expressed as a fusion protein containing 36 amino acids of *E.coli* $\beta$ glucuronidase at the amino terminus followed by the entire coding sequence of tat. These additional sequences have been shown to confer stability at the protein as well as at the RNA level to various eukaryotic gene products expressed in *E. coli* (See referenced patent). at the protein as well as at the RNA level to various eukaryotic gene products expressed in *E. coli* (See referenced patent).

EXAMPLE 2

Extract preparations from both *E. coli* and baculovirus systems containing tat protein was determined by SDS polyacrylamide gel electrophoresis (not shown) as well as by Western Blot analysis (FIG. 2). The baculovirus tat migrated as a doublet of 14.5 and 15.5 kDa. The *E. coli* produced fusion protein as slightly larger, migrating at 17 kDa in a minor band at 15.5 kDa. The doublet observed in the baculovirus tat preparation may represent limited proteolysis or, alternatively, may represent two forms of the tat protein at the conformational level, or may result from covalent modification (e.g. phosphorylation). While this may apply to the 15.5 kDa polypeptide in the *E. coli* preparation, this faster migrating species may correspond to internal initiation at the authentic tat AUG codon. The purity of the baculovirus tat and *E. coli* tat preparations are estimated at 5 and 50 percent, respectively, as determined by visualization of stained polyacrylamide gels (data not shown).

EXAMPLE 3

To test ability of the recombinant tat proteins to transactivate HIV-1 LTR directed gene expression, the *E.coli* and baculovirus protein preparations were introduced by "scrape-loading" procedure into HeLa cells, stably integrated with the HIV-1 LTR linked to the bacterial chloramphenicol acetyl transferase gene (Hela/LTR-CAT). Both baculovirus and *E. coli* tat preparations were functionally active as determined by the induced level of CAT activity (FIG. 3). As controls, baculovirus gp160 infected cell extracts prepared the same way as the baculovirus tat preparation and mock treated with Hela/LTR-CAT cells showed no significant increase in LTR directed gene expression.

EXAMPLE 4

In an effort to study the potential association of tat with the TAR sequence present at the 5' region of HIV RNAs, a construct was designed which substituted the upstream LTR sequences with the bacteriophage T7 polymerase promoter (FIG. 4). The plasmid T7-TAR-CAT was digested with Hind III. This plasmid directs the synthesis of an 80 nucleotide transcript in vitro with T7 polymerase and nucleoside triphosphates. The T7 enzyme initiates faithfully at the HIV-1 cap site, as determined by primer extension of in vitro synthesized RNA (data not shown).

EXAMPLE 5

$^{32}P$ labeled 80 nt transcript in RNA gel mobility shift experiments were used to assay the direct binding of recombinant tat. Retarded band representing protein-RNA complexes were detected using the *E. coli* tat and baculovirus tat extracts, but not with baculovirus gp160 or baculovirus rev preparations (FIG. 5). The RNA complex formed using the *E. coli* tat migrated at exactly the same position as one of the complexes formed with the baculovirus tat. An additional complex was seen with baculovirus tat migrating an intermediate distance between the probe and upper band. (The nature of the two complexes is not clear, but could correspond to the two bands observed for baculovirus tat in the Western Blot. Alternatively, the additional band may represent a variation in the RNA-protein complex, or a monomer or dimer formation.) No differences were observed in the binding experiments using capped and uncapped RNAs (data not shown).

EXAMPLE 6

Specificity of binding reaction was determined by the RNA gel mobility shift assay using wild type and mutant transcripts (FIG. 6). A four base pair deletion was generated at the SSTI site, +35 to +38 nucleotides relative to the transcription initiation site, in the T7-TAR-CAT plasmid. The resulting plasmids contained a deletion overlapping the loop and stem. This mutation has been shown to abolish transactivation in the HIV-1 LTR-CAT background. Unlike the wild type transcript, the deleted (Δ S) transcript failed to form a stable complex with recombinant tat protein in the gel mobility shift assay. The binding to RNA was completed by excess unlabeled wt TAR RNA (FIG. 7).

DISCUSSION

The sequence requirements for binding correlate with the sequences requirements for transactivation, suggesting a correlation between binding of tat protein and TAR. Since the binding of the tat protein to TAR effects transactivation, comparative testing of compounds for the effect on tat protein-TAR RNA binding can be used as a screen to evaluate compositions for activity against the HIV-1 gene expression regulated by the tat. The method for evaluating inhibitory effect of the substance would, therefore, consist of the following steps:

1) preparing a mixture of the test substance and tat protein;
2) adding to the preparation which is the product of step (1) a composition of matter containing TAR RNA; and
3) observing the product prepared in step (2) for evidence of binding between TAR RNA and tat protein.

While the use of $^{32}p$ labelled 80nt transcript is used in an RNA gel mobility shift experiment to assay direct binding, the invention should not be construed as limited to the embodiment. For example, either the protein or the TAR RNA could be labelled with labels known to those of ordinary skill in the art.

The conditions under which the assay to test for binding is run will be adjusted depending on the substance being tested for effect on tat protein TAR RNA binding. As indicated in the samples, the rate at which tat or any complex of that protein migrate on a gel may depend on the vector system in which the components were produced.

The data clearly indicated specific and stable binding of tat to TAR RNA. A mutation within TAR which abolished transactivation also precluded stable complex formation, suggesting that binding of tat to RNA is a functional step in the transactivation pathway. The assay system can be used as a tool in dissecting the sequence requirements for the tat response as well as a convenient system for screening of compounds which would block tat activation of the HIV gene expression.

The specificity of tat interaction with RNA may be further increased in the natural setting by interaction with the transcription complex, other cellular factors, or RNA polymerase II.

What is claim is:

1. A test system, consisting essentially of a first solution comprising cell from tat protein and a second solution comprising cell free TAR RNA, wherein upon mixing of said first solution and said second solution, said tat protein and said TAR RNA are capable of associating with one another and wherein such association is capable of providing a measurable result.

2. A cell free composition of claim 1 in a gel.

3. A method of evaluating the inhibitory effect of a substance on tat-protein TAR RNA binding comprising the steps of:

1) preparing a mixture of the test substance and tat protein;
2) adding TAR RNA to the preparation of step 1, wherein the tat protein and the TAR RNA are capable of associating with one another and wherein each is present in quantities sufficient to provide a measurable result in the event of binding between tat and TAR; and
3) observing the preparation of step 2 for evidence of binding between TAR RNA and tat protein.

* * * * *